US007052835B2

(12) United States Patent
Asai et al.

(10) Patent No.: US 7,052,835 B2
(45) Date of Patent: May 30, 2006

(54) METHOD OF SCREENING A GENE

(75) Inventors: Satoshi Asai, Tokyo (JP); Toshihito Nagata, Tokyo (JP); Yasuo Takahashi, Tokyo (JP); Yukimoto Ishii, Tokyo (JP); Koichi Ishikawa, Tokyo (JP)

(73) Assignee: Nihon University, School Juridical Person, Tokyo (JP)

( * ) Notice: Subject to any disclaimer, the term of this patent is extended or adjusted under 35 U.S.C. 154(b) by 347 days.

(21) Appl. No.: 10/042,407

(22) Filed: Jan. 8, 2002

(65) Prior Publication Data

US 2003/0152928 A1  Aug. 14, 2003

(30) Foreign Application Priority Data

Apr. 11, 2001  (JP) .............................. 2001-112367

(51) Int. Cl.
C12Q 1/68 (2006.01)
C12P 19/34 (2006.01)

(52) U.S. Cl. ........................ 435/6; 536/24.3; 536/24.33
(58) Field of Classification Search .................... 435/6; 536/23.1, 24.3, 24.32
See application file for complete search history.

(56) References Cited

U.S. PATENT DOCUMENTS 5,597,692 A * 1/1997 Coghlan et al. ................ 435/6
5,990,078 A * 11/1999 Toran-Allerand ............... 514/2
6,027,890 A * 2/2000 Ness et al. ..................... 435/6
6,342,495 B1 * 1/2002 Joly et al. ................... 514/221
6,670,138 B1 * 12/2003 Gonzalez-Zulueta et al. .... 435/7.1

FOREIGN PATENT DOCUMENTS

WO  WO 01/62965 A2 * 8/2001

OTHER PUBLICATIONS

Nagata et al. The localization of peroxisomal Acyl-CoA Oxidase mRNA by in situ hybridization methos with light and electron miscroscopic radioautography. Journal of Histochemistry and Cytochemistry (1992) vol. 40, No. 4, p. 591.*

Schena et al. Quantitative monitoring of Gene expression patterns with a complementary DNA microarray. Science (1995) vol. 270, pp. 267-270.*

Asai S. Analysis of Morphology by in situ Hybridization following Genome Wide Screening. 73rd Japanese Biochemistry Society Annual Meeting [in Japanese] (with Applicants' English translation/explanation). Oct. 13, 2000.

Asai S. Status of Gene Expression Analyses on Cerebral Ischemia Disease Using GeneChip System. 23rd Japanese Molecular Biology Annual Meeting [in Japanese] (with Applicants' English translation/explanation). Nov. 25, 2000.

Asai S. et al. Acute Ischemic Change of mRNA Expression in the Hippocampus by GeneChip Array Analysis: A Starting Point for Post-Genome Strategy. 74th Japanese Pharmacological Society Annual Meeting. Mar. 21, 2001.

* cited by examiner

Primary Examiner—Kenneth R. Horlick
Assistant Examiner—Cynthia Wilder
(74) Attorney, Agent, or Firm—Jones Day

(57) ABSTRACT

The present invention provides a method of screening genes based on expression information differing from gene expression information obtainable by DNA chip/DNA microarray techniques. The method of screening genes comprises performing in situ hybridization in respect of a tissue or cell sample from an organism using a probe which specifically hybridizes with mRNA and/or expression sequence tag being a product of gene expression, and examining localization of the mRNA and/or expression sequence tag in the tissue or cell.

9 Claims, 12 Drawing Sheets

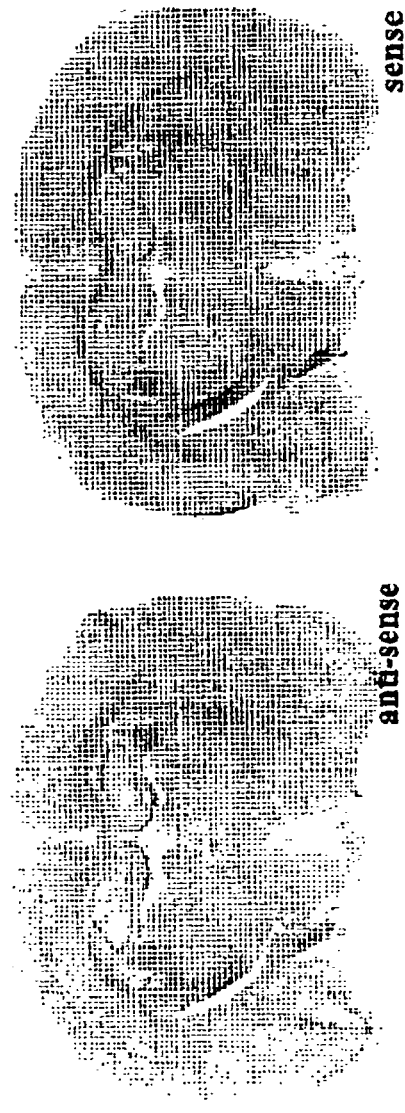
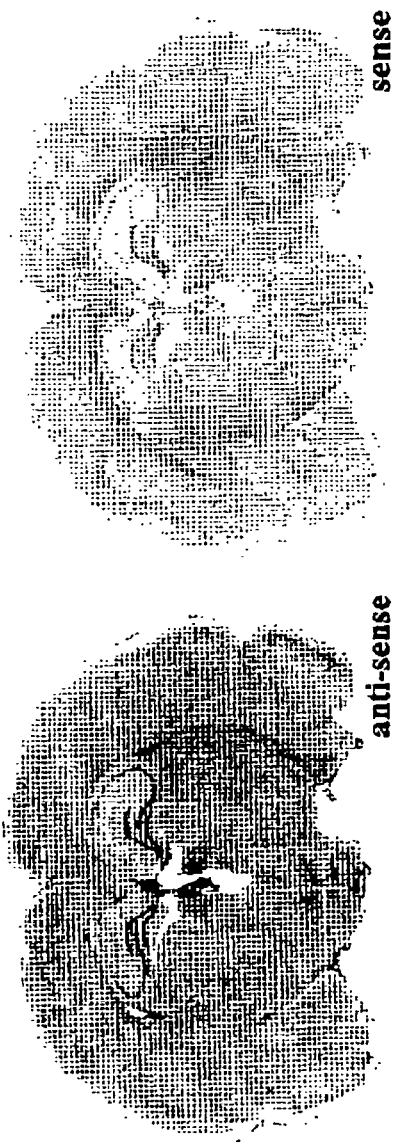
FIG.8 Heat Shock Protein (HSP 70): Control Rat Brain / Heat Shock Protein (HSP 70): Ischaemic Rat Brain

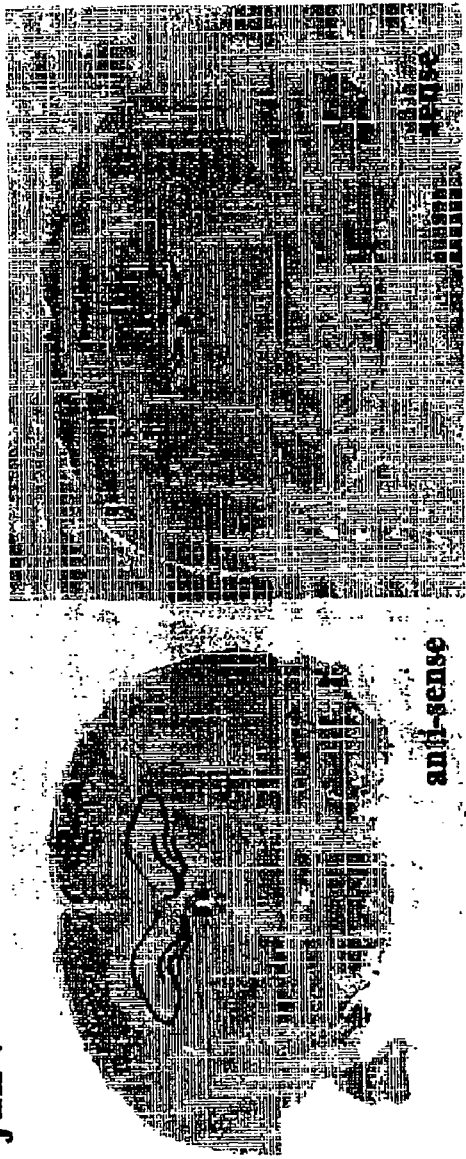
FIG.9

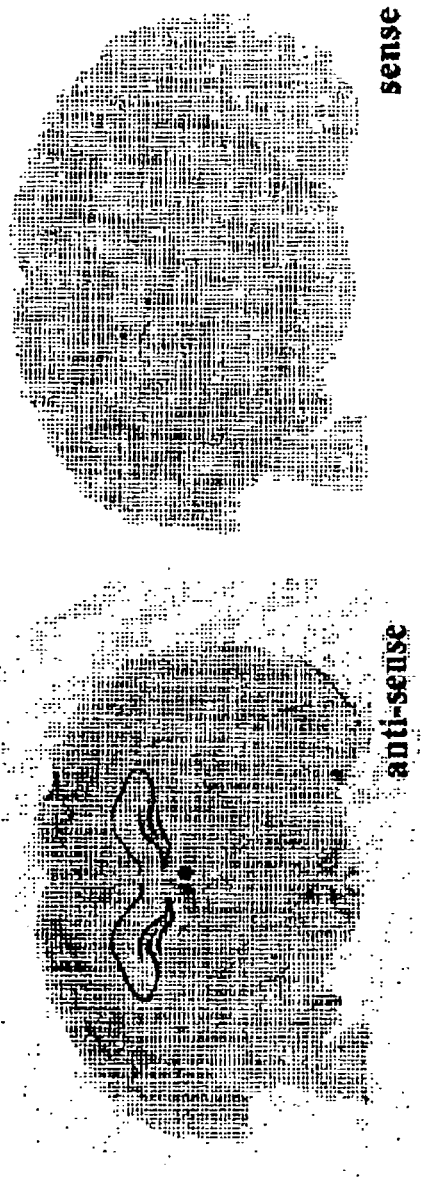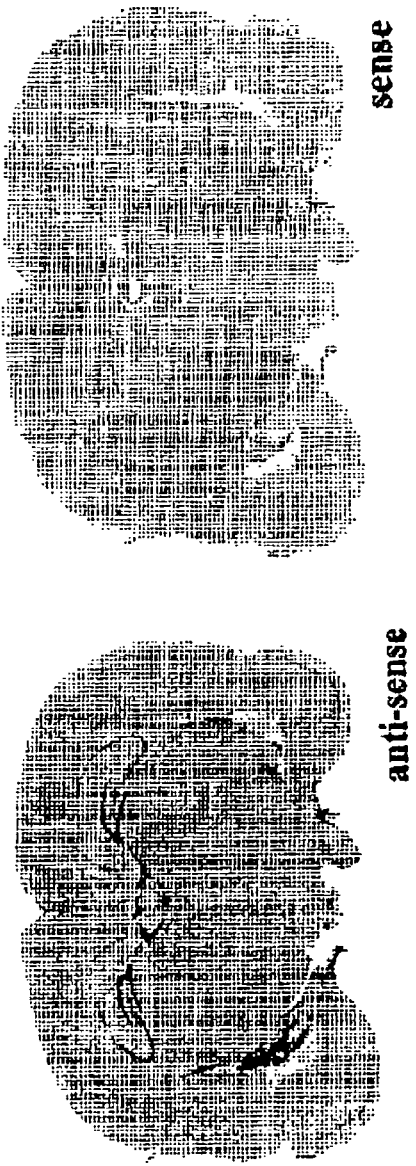
FIG.10  EST 1 : Control Rat Brain    EST 1 : Ischemic Rat Brain

FIG.11

 
FIG.12  EST 2 : Control Rat Brain    EST 2 : Ischemic Rat Brain

METHOD OF SCREENING A GENE

This application claims priority benefit, under 35 U.S.C. §0 119(a), of Japanese Patent Application No. 2001-112367, filed Apr. 11, 2001.

TECHNICAL FIELD

The present invention relates to a method of screening a gene.

BACKGROUND ART

Recently, a broad outline of human genome analysis has been published and the focus of research is shifting from genome analysis which involves analysis of genome DNA sequence information, to expression (functional) analysis which involves analysis of gene expression. At present, among expressed genes including expression sequence tags (EST), there are few whose function is understood even if the sequence thereof is already known.

In gene expression analysis, techniques for performing analysis with large samples at high speed and good efficiency (high throughput techniques) are required. DNA chip/DNA microarray techniques can provide expression information concerning several tens of thousands of genes in one cell, and are succeeding in effecting high throughput in gene expression analysis experiments.

For example, by using DNA chip/DNA microarray techniques, it is possible to identify genes, the expression level of which changes together with changes in a disease condition. If the expression level of a particular gene correlates highly with the prognosis of a patient, then the expression information concerning this gene can be used as an effective indicator in drug creation.

However, expression information obtainable by DNA chip/DNA microarray techniques does not enable prediction of drug efficacy.

DISCLOSURE OF THE INVENTION

An object of the present invention is to provide a method of screening genes based on expression information which differs from gene expression information obtainable from DNA chip/DNA microarray techniques.

Even if with DNA chip/DNA microarray techniques, the presence or absence of expression, or level of expression of a gene in each cell can be understood, this information does not necessarily immediately lead to drug creation. The present inventors considered that it was possible to screen a target from among numerous genes or expression sequence tags that have been cloned but whose functions are unknown, from the point of view of localization of expression in tissue or cells of an organism. Further, using an in situ hybridization method, and by examining localization of expression in the tissues of an organism, the present inventors have succeeded in establishing a system for screening a target gene, thereby completing the present invention.

That is to say, the present invention provides a method for screening a gene, by performing in situ hybridization with tissue of an organism, or a cell sample using a probe that specifically hybridizes with an mRNA and/or an expression sequence tag being a product of gene expression, and examining the localization of the mRNA and/or expression sequence tag in the tissue or cells.

By the method of the present invention, it is possible to screen targets by not only screening genes which are structural units bearing genetic information but also expression sequence tags (EST) which do no more than bear fragmentary genetic information.

In the method of the present invention, mRNA and/or expression sequence tags being the products of gene expression may be ones which express in cultured cells or tissue. The mRNA and/or expression sequence tags being the products of gene expression can be those the expression of which has been confirmed with a DNA chip or DNA microarray. Further, mRNA and/or expression sequence tags being the products of gene expression, may be products, the expression level of which alters in response to an event.

Herein, an "event" refers to any kind of change occurring internally or externally in an organism, and examples thereof include ischemia, tumor, and administration of a drug.

In the method of the present invention, a gene and/or expression sequence tag which has been cloned but which is of unknown function can be used.

Herein, "of unknown function" or "the function of which is unknown" refers to any of physico-chemical function, biochemical function or physiological function having not been analyzed. Here, function on a physicochemical level includes properties relating to intermolecular interactions. For example, where a protein encoded by particular gene binds with DNA, the gene thereof can be said to encode a protein having a function of binding with DNA (a function at a physico-chemical level). Function at a biochemical level includes properties involved in biochemical processes. For example, a protein encoded by a particular gene binds with a gene promoter region within DNA, and it is clear that this activates transcription, the gene thereof can he said to encode a transcription activation factor (function on a biochemical level). Function at a physiological level included roles in organisms, tissues or cells. For example, if a gene encoding a protein is disrupted, and a mouse with no front legs is born, this protein can be said to have a function involved in the differentiation of front legs (function at a physiological level).

By a single screening according to the method of the present invention, the localization of at least two different types of mRNA and/or expression sequence tag may be examined in one type of the same tissue or cells. By a single screening according to the method of the present invention, it is possible to examine localization of, for example, two or more differing mRNA and/or expression sequence tags in the same single type of tissue or cell. For this, it is preferable to technique for performing a plurality of stainings simultaneously (double stain, triple stain, sky fish, etc.) by changing the fluorescence wavelength of the probe, and changing the secondary antibody.

Or, further, by a single screening according to the method of the present invention, localization of one type of mRNA or expression sequence tag in at least two different types of tissue or cell may be examined. By a single screening according to the method of the present invention, localization of one type of mRNA or expression sequence tag can be examined in, for example, two or more types, preferably, 10 to 20 types of different tissue or cell.

The method of the present invention can be used to screen for a gene encoding a substance effective as a medicament. For example, from the fact that expression of a gene is localizes at a specific site, by considering distribution within a tissue or cell, it is possible to predict the effect of that gene as a drug.

Further, the method of the present invention can be used to screen for a gene related to a disease condition. For example, by using a disease model animal, transgenic animal, knock-out animal or the like, it is possible to more effectively select a useful probe by contrasting probe localization and pathogenic site.

Further, the method of the present invention can be used to examine the function of a gene or expression sequence tag, which has been cloned but which is of unknown function. By knowing organ-specific localization within cells or within tissues, it is possible to predict distribution of protein expression and probe targeting can be performed more efficiently.

Further, the present invention provides a method of monitoring gene expression which comprises collecting a tissue or cell sample from an organism each before and after occurrence of an event, performing in situ hybridization in respect of the sample using a probe which specifically hybridizes with mRNA and/or expression sequence tag being a product of gene expression, and examining change in localization of the mRNA and/or expression sequence tag in the tissue or cell. The tissue of cell sample may be collected from an organism at at least two different points in time after occurrence of an event.

The method of screening genes according to the present invention involves the innovative approach of selecting a gene from the novel point of view of localization of a gene and/or expression sequence tag in the tissue or cells of an organism, and is useful in screening a target gene.

Further, since the method of screening genes according to the present invention involves the selection of genes from the above-described morphologic point of view, it can lead research and development of drugs in a more correct direction. As a result, time and effort required for drug, research and development can be reduced and costs can be lowered.

The method of monitoring gene expression of the present invention can be used in searching for a gene related to a condition, in searching for gene or EST which has been cloned but the function of which is unknown, in genome drug development, etc.

After genome wide screening, according to the method of the present invention, it is possible to screen a target gene by performing large scale screening from the point of view of localization in tissue or cells of an organism.

This will be explained in more detail by taking as an example the case of a search for a drug useful in effecting recovery from damage due to ischemia. In an ischemia model animal, a gene having an expression level that differs between before and after an event, being ischemia, is detected with a DNA microarray or DNA chip (for example, the high-density oligonucleotide array GENECHIP™ (U.S. Affymetrics, Inc.)) (genome-wide screening). Next, sequence information of the genes having expression levels that differ between before and after the ischemia event is obtained, by linking data obtained by DNA microarray or DNA chip with bioinformatics. Based on this sequence information, a probe for in situ hybridization is designed, and prepared. Thereafter, in situ hybridization is used to examine how this gene is distributed in what types of tissue in an organ in which ischemia occurred (for example, brain, liver, etc.). In situ hybridization operations, can be either manual or automatic. For example, by using Ventana HX system (Ventana Medical Systems, Inc.) which realizes a complete automation of in situ hybridization, results with good reproducibility can be obtained in a short time. From the results of in situ hybridization, it is possible to screen a gene which has a tissue distribution thought to be suitable for its use a drug. For example, where a drug for memory recovery is being sought, a gene having expression localized in the hippocampus is selected. Further, where a drug which suppresses inflammation is being sought, a gene the, expression of which is distributed in the entire brain is selected.

Below, a mode for carrying out the present invention through combination of gene expression analysis by DNA chip and in situ hybridization, will be explained.

1. Gene Expression analysis by DNA chip

A method of analysis using conventional blotting techniques, wherein hybridization is performed simultaneously in respect of a plurality of probes arranged in an array, is generally referred to as array technology (The chipping forecast. Nature Genetics, supplement vol. 21, (1999)). In particular, where an array is prepared with probes as spots in an array form having a diameter of less that 1 mm, this is referred to as a microarray or chip, and arrays having probes constituted by DNA are referred to as "DNA chips". At present, methods realizing this array technology include a method where cDNA is spotted on a filter to form an array, a method here cDNA or synthetic DNA is spotted on a slide glass, and further methods such as the hi-density oligonucleotide array GENECHIP™ (U.S. Affymetrics, Inc.) (Lockhart, D. J. et al. (1996), Expression monitoring by hybridization to high-density oligonucleotide arrays. Nature Biotechnology 14, 1675–80; Wodicka, L. et al. (1997) Genome-wide expression monitoring in Saccharomyces cerevisiae. Nature Biotechnology 15, 1359–67). In GENECHIP™, spotting technology differs from that of other DNA chips. To distinguish between this and other methods, this method per se is referred to by the trademark "GENECHIP™". With GENECHIP™, it is possible to perform both genome analysis for analyzing genome DNA mutation, and expression analysis for analyzing gene expression. However, in the present invention, expression analysis is performed.

1.1 Principle and Summary

In the GENECHIP™ technique, the method of spotting DNA probes on the chip differs from that of other DNA chips. In conventional methods, a DNA probe directly excised from an organism was spotted on a foundation. In contrast, with the GENECHIP™ technique, DNA is synthesized as fragments of 18 to 25 mer using a photochemical reaction in a step resembling semiconductor manufacture techniques. As a result, several million probes having 18 to 25 mer nucleotide sequences are immobilized on a 50 or 24 μm square probe cell (this is referred to as a "tile").

As a result of such differences in chip manufacture, properties such as the following are produced:

(1) With a probe size of approximately 18 to 25 mer, there is a phenomenon where a mismatch probe having a single nucleotide substituted in the middle of the probe will not readily hybridize (Goto, et al. (1997) Gene Diagnosis by Affinity Sensor BIACORE—theory and application—Clinical pathology 45, 224–28). Exploiting this, it is possible to perform confirmation by perfect match and mismatch (probe pair) for each probe arranged on each tile. By an operation such as this, it is possible to eliminate false positive signals arising from non-specific binding from the fluorescence intensity signals obtained by the hybridization experiment, thus the system enables accurate measurement of signal strength arising from true probes having a perfectly matching nucleotide sequence (Lipshutz, R. J. et al. (1999) High density synthetic oligonucleotide arrays. Nature Genetics supplement, volume 21, January)). Further, assisted by the shortness of the probe size and sample size, not only non-specific hybridization, but also the background signal can be eliminated, thereby increasing quantitivity. Further, the synthesized oligonucleotide probe set is determined based on a coding region, a unique nucleotide sequence, and hybridization ability of the target gene.

Realized as a direct extension of these techniques is genome mutation analysis. This method is a groundbreaking method involving detection of a difference of a single nucleotide with p53, HIV, P450, SNP chip, etc. Since analysis is of a difference of one nucleotide sequence, a probe cell having 4 to 5 probes corresponding to the four types of nucleotide G, A, T, C, for the site to be analyzed, and where necessary a probe having this site deleted, is used.

(2) GENECHIP™ is constituted by a hybridization oven for binding the sample to the probes on the chip, a Fluidic Station for washing and labeling, a Gene Array scanner for, reading fluorescence emissions, and a computer system for processing and analyzing the read information. Further., since experimental conditions from sample preparation to data collection are optimized by using a pre-existing kit, it is possible to obtain data with high reproducibility. Since the expression levels of several thousand genes are precisely assayed on a chip, arranging probes for *E. coli* genes on the chip and mixing a fixed amount of cRNA derived from *E. coli* genes in with the sample as a control (spiking) enables quantitivity of the genes within the sample to be raised, as well as providing a check on the precision of the operating process of the experiment. Further, by using in conjunction with the results of measurement using probes for housekeeping genes such as GAPDH and actin, comparative analysis of a plurality of different experimental results can be conducted, and reliable data having a wide dynamic range, can be obtained with high sensitivity without the user being troubled by examination of experimental conditions, etc.

1.2 Items to be Prepared

GENECHIP™ is a comprehensive system encompassing steps from sample preparation to data analysis, and is almost fully completed. Consequently, for reagents, kits, etc. to be used in each step, the following, which are recommended by Affymetrics, Inc., are recommended here.

Isolation of total RNA
   TRIzol Reagent (Gibco BRL Life Technologies)
   RNeasy Total RNA Isolation Kit (QIAGEN)
Isolation of Poly(A)$^+$ mRNA
   Oligotex Direct mRNA Kit (QIAGEN)
   Oligotex mRNA Kit (QIAGEN)
cDNA synthesis
   Superscript Choice System (Gibco BRL Life Technologies)
   T7-(dT)$_{24}$ Primer (GENSET Corp.)
Synthesis of Biotin labeled cRNA (In Vitro Transcription, IVT)
   RNA Transcript Labeling Kit (Enzo)
IVT cRNA washing and quantification
   RNeasy Mini Kit (QIAGEN)
   CHROMA SPIN—100 columns (CLONTECH)
Buffer for fragmentation of labeled cRNA
   200 mM Tris-acetate, pH 8.1, 500 mM KOAc, 150 mM MgOAc
Internal standard substance (Expression Control Clones)
   pglbs-bioB, pglbs-bioC, pglbs-bioD, pglbs-cre 1.3 Protocol The sequence of operations is as follows:

Step 1—Extract approximately 2 μg of Poly (A)* mRNA from the sample.

Step 2—Perform cDNA synthesis with reverse transcriptase.

Step 3—Mass produce biotin-labeled cRNA by in vitro transcription, and purify.

Step 4—Subject labeled cRNA to DNase treatment, or heat treatment in the presence of magnesium ions thereby fragmenting to a size of approximately 50 mer.

Step 5—After labeling a known internal standard (spiking), add to sample, and pour onto Chip.

Step 6—Perform hybridization in an oven, and perform labeling in a Fluidic Station.

Step 7—Import chip information with GeneArray Scanner.

Step 8—Perform data processing and analysis using a Bioinformatics (biological information processing) system.

1.4 Bioinformatics

Since a large amount of data can be obtained with GENECHIP™, to use it efficiently, so-called bioinformatics (Bioinformatics) techniques are required. For this purpose, in GENECHIP™, as bioinformatics tools, the proprietary GENECHIP™ Laboratory Information Management System (LIMS™) and GENECHIP™ Expression Data Mining Tool (EDMT™) are provided therewith, and these enable data to be input into a SQL compliant database in a format determined by an open consortium for standardizing gene-related analysis techniques (GATC), and linked to gene information databases (GenBank, etc.) published on the internet. However, since bioinformatics per se is still in a developmental stage, there are cases where data analysis with known systems is insufficient. In small and medium scale research facilities, there arises the need to separately file and analyze the databases of a few individuals, and use other analysis programs to perform data processing, graphing, and statistical calculations. Here, the present inventors naturally access an LIMS-SQL server and use an EDMT-like tool to process data, store individual data in a GATC compatible extension database, and using Gene Spring (U.S. Silicon Genetics, Inc.) perform clustering, tabulation, searches, and information database searches. Further for statistical calculations, and analysis of the functional hierarchy of individual genes, the present inventors use Stingray (U.S. Affymetrics, Inc.).

2. Examination of Localization of Expressed Genes by In Situ Hybridization

The present inventors performed in situ hybridization with fresh frozen slices. Fresh frozen slices have the strength that compared with other tissue samples such as paraffin immobilized (issue and tissue embedded after immobilization, a signal can most easily be obtained. This is because permeability into the probe tissue is high.

Table 1 shows a flow chart for in situ hybridization using a fresh frozen sample. The process is explained below in accordance with the flow chart.

TABLE 1

Flow chart of in situ hybridization using Fresh Frozen Sample

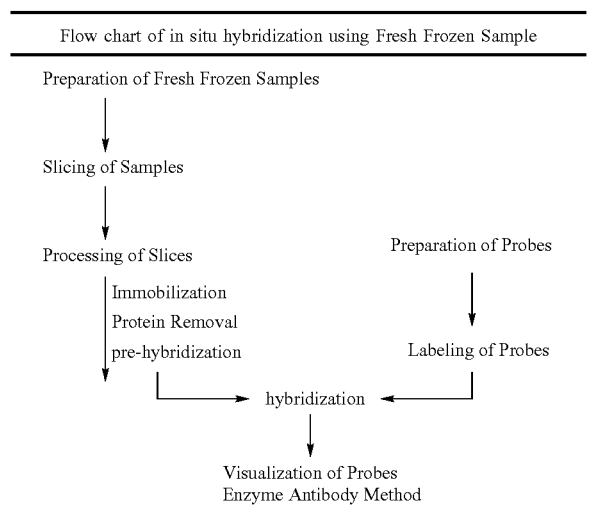

2.1 Preparation of Fresh Frozen Slices

Since a fresh frozen slice is a raw sample, it is easily compromised by RNase, and to proceed with the experiment, it is necessary to perform the experiment in as near an RNase-free state as possible, and particular attention must be made to preserving the mRNA in the tissue.

(1) Analyte

A sample (e.g. brain or liver) is excised from an experimental animal. Gauze that has been soaked in physiological saline solution is placed on a clean sterilized plate, and the sample is wrapped to prevent drying. Further, where there is a thick coat of film or where venous tissue or interstitial tissue is included, since it is difficult to obtain thin slices, these are preferably cut away.

(2) Embedding tissue

A small amount of OCT compound (manufactured by Milles Lab) is placed at the bottom of a plastic vessel for embedding, or of aluminum foil molded into a cylinder. Tissue cut to an appropriate size is placed thereon, and OCT compound is injected from above such that the tissue comes to the center. These are then immersed in acetone which was previous placed in dry ice, to quick freeze. After freezing, these are transferred to a plate containing dry ice, and after embedding of the tissue has been completed, stored in a freezer at −80° C.

(3) Thin slicing of tissue

Slices, 10 μm in size, are cut using a cryostat. After cutting, slices are adhered to 3-aminopropyl triethoxy silane (ASP)-coated slide glasses. A method of preparing an ASP-coated slide glass is shown in Table 2.

TABLE 2

Method of Preparing APS coated slide glass

1. Dissolve APS (Sigma) in acetone to 1 to 2%.
2. Place slide glass in rack, and immerse in APS solution for 5 to 10 seconds.
3. Wash gently with acetone.
4. Wash with DEPC processed distilled water*
5. Air dry overnight within a hood Note:
*DEPC processed distilled water: Solution in which RNase has been inactivated, which is prepared by adding 0.1% DEPC (diethylpyrocarbonate) to distilled water, stirring well in a stirrer, and placing in an autoclave after allowing to stand overnight.

After tissue is adhered to the slide glass, it is immediately dried using cooled air.

(4) Preservation of tissue

After slicing thinly, immobilization is performed using 4% paraformaldehyde. The in situ hybridization step may be performed immediately thereafter. If in situ hybridization is not performed immediately, the slice is dried for 30 minutes or more with cooled air, placed in a slide glass rack, sealed with vinyl tape, and stored at −80° C.

With extra tissue remaining after slicing, an OCT compound is placed on the cut face thereof, processing to avoid drying of the tissue is performed, and the tissue is stored at −80° C.

(5) Examination of remaining RNA in the tissue

No matter what kind of tissue, mRNA within the tissue will be destroyed by the various operations, and evaluation of the remaining RNA is important. Methods for evaluation are broadly divided into special staining methods and in situ hybridization methods. A special staining method involves staining the whole of the RNA including mRNA with acridine orange or methyl green/pyroline Y stain. Methods for evaluating remaining RNA with in situ hybridization, involve performing in situ hybridization in respect of β-actin, poly-A RNA, and 28 S ribosome RNA (rRNA). In the case where RNA staining provides a negative result, the RNA is judged not to be present in the tissue, and thus the tissue is unsuitable for in situ hybridization. On the other hand, where a positive result is obtained by RNA staining, unless the in situ hybridization treatment is performed properly, a positive finding cannot be obtained. For example, cases are known where the probe cannot reach the target mRNA. Therefore, a positive control is essential for in situ hybridization. β-actin is used as an internal control in procedures such as Northern blot, however, its level often varies according to conditions such as cell proliferation. A probe for performing in situ hybridization with the poly A of mRNA has, in comparison to a normal probe, a totally different GC-content, and the Tm value differs, so it becomes necessary to change the in situ hybridization conditions. As a result, this hybridization cannot be performed simultaneously with normal in situ hybridization, and is therefore not generally employed. In contrast, 28S rRNA is distributed widely in all cells, and its production level is very constant. Further, with the 28S rRNA oligo probe employed by Yoshii, et al. (Yoshii A, et al., J Histochem Cytochem, 43:321–327, 1995), it is possible to use the same probe in different species enabling in situ hybridization to be performed with the same probe on experimental model animals to humans.

2.2 In situ hybridization

Below, processing of the probe and slice will be explained.

(1) Preparation of probe and labeling (1-1) Preparation of probe

As a probe, a double-stranded DNA (dsDNA), oligonucleotide (approximately 20 to 40 nucleotides in length), or RNA probe can be used.

To prepare an RNA probe, it is preferable to prepare a template, perform in vitro transcription, and confirm the purity and concentration of the RNA probe.

In the preparation of templates, there are the following cases: (a) a case where a plasmid is adopted as a template, (b) a case where a PCR product from a plasmid is adopted as a template, and (c) a case where a PCR product from cDNA is adopted as a template. Case (a) where a plasmid is adopted as a template is most common, however, the present inventors have been successful with the method of case (c). In the method of case (a), first, a probe DNA fragment is incorporated into a plasmid having promoters such as SP6, T3, T7, etc. (approximately 3 to 4 weeks). Plasmid DNA is cleaved with restriction enzymes and linearized. Next, to make it RNase-free, the linearized plasmid DNA is processed with proteinase K. In the method of case (c), mRNA is extracted from frozen tissue, and cDNA is synthesized. PCR is performed (approx. 7 to 10 days) using primers including an RNA polymerase promoter sequence, upstream or downstream thereof (since both antisense and sense probes are prepared). For example, a T7 promoter sequence can be incorporated at the 5' terminus of the 3'-side primer for preparation of the antisense probe, and a T7 promoter sequence may be incorporated at the 5' terminus of the 5'-side primer for preparation of the sense probe.

In vitro transcription can be performed using a commercially available kit (e.g. AmpliScribe™ T7 Transcription Kit (EPICENTRE TECHNOLOGIES)).

Purification of the reaction product (RNA probe) can be performed using a commercially available kit (e.g. RNeasy minikit (QIAGEN)).

Absorbance of the purified reaction product is measured and RNA concentration calculated.

(1-2) Probe labeling

Labeling techniques include radioactive labeling anti non-radioactive labeling. In radioactive labeling 35S is widely used. Non-radioactive labeling techniques include methods of labeling with digoxigenin which is a hapten, or biotin, etc. and the T—T dimer method which involves formation of dimers of thymine which is a nucleotide of nucleic acids by irradiation with UV (Koji T, et al. Acta Pathol Jpn, 40: 793–807, 1990).

Hapten labeling can be easily performed using a commercially available kit. In the case of a dsDNA probe, this can be labeled with digoxigenin by using a random primer method (e.g. DIG DNA labeling Kit manufactured by Boehringer). An oligonucleotide probe can be digoxigenin labeled easily using DNA Tailing Kit (manufactured by Boehringer) and an RNA probe can be digoxigenin labeled easily using a DIG-RNA Labeling Kit (manufactured by Boehringer).

Whether or not labeling was effected, can be examined by developing on a membrane. That is, the labeled probe is step-wise diluted by factors of 10, to prepare an approx. 10 ng/μl to 1 pg/μl solution. This is dripped onto nylon (cellulose) membrane, 1μl at a time and allowed to dry. Thereafter, it is allowed to develop using a method that will allow actual development in situ hybridization (using alkali-phosphatase or peroxidase-labeled anti-hapten antibody). If the label is sufficient then the label should develop with good sensitivity. In the case where there is no development, or where sensitivity is poor, this means that the label is insufficient. In this case, since a kit contains an already labeled positive control, this is confirmed with simultaneous staining. Further, a digoxigenin assay strip (Boehringer 1669958) is commercially available with which it is possible to simply check whether or not the probe has been well labeled. Biotin and digoxigenin are frequently used as haptens for labeling. The kidney, liver, and muscle, etc. include large amounts of endogenous biotin, and where fresh frozen tissue is used, considering background after staining, digoxigenin is the more preferable.

Further, in addition to examining whether or not probes have been labeled, whether or not hybridization is properly occurring among sense-antisense nucleic acids is examined by performing dot hybridization on a membrane. First, a serial dilution of unlabeled sense probe is prepared, dripped onto a nylon membrane and allowed to dry. This is then allowed to hybridize with a labeled antisense probe and thereafter, developed using the enzyme antibody method in the same manner as described in the below-described in situ hybridization with tissue.

(1-3) Tissue processing and hybridization

1. Rehydration

Where slices which had been adhered to ASP coated slide glasses were being stored at −80° C., after removing the slide glass box containing the slices from the freezer, the slide glass box is placed while remaining sealed in a 37° C. heater, and opened after warming for approx. 60 minutes. After placing in a slide glass rack, the slides are soaked in PBS for 3 minutes to rehydrate.

2. Immobilization

Tissue slices are immobilized in 4% paraformaldehyde/PBS solution for approx. 15 minutes at room temperature. After immobilization, tissue slices are placed in a staining vat containing PBS, a while shaking on a shaker are wash for 3 minutes, 3 times.

3. Protein removal

With unprocessed tissue, since probe permeability is insufficient, protein removal treatment of the tissue is required. In the protocol here, protein removal is performed by hydrochloric acid and proteinase K. First, as a hydrochloric acid treatment, tissue is immersed in a staining vat containing 0.2N HCl (diluted with distilled water), for 10 to 20 minutes, at room temperature. Thereafter, PBS washing is performed for 3 minutes, 3 times, while shaking on a shaker. Next, proteinase K (molecular biology use) treatment is performed. A solution having it final proteinase K concentration of 0.5 µg/ml/PBS is prepared, and previously left in a 37° C. water bath for 30 minutes. The solution is allowed to penetrate into the slice at 37° C. for 5 to 15 minutes, and thereafter the slice is washed with PBS for 3 minutes, 3 times on the shaker.

4. Post-immobilization

Tissue loosened by protein removal is tightened. In particular, in the case of fresh frozen slices, this is necessary from preservation of forth. Tissue slices are immobilized in 4% paraformaldehyde/PBS for 5 to 10 minutes at room temperature. Note that after post-immobilization, slices are washed with PBS to neutralize aldehyde remaining in the sample, and may be immersed twice in 2 mg/ml glycine/PBS for 15 minutes. Thereafter washing is performed.

5. Pre-hybridization

Tissue slices are immersed in pre-hybridization solution (4×SSC/3×Denhardt's solution/20% formamide) at room temperature for 30 minutes (slices may be immersed for in excess of 1 hours). By performing this processing, the hybridization solution takes to the slices more easily.

6. Hybridization

A hybridization solution (4×SSC/50 mM sodium phosphate buffer solution (pH 8.0)/5×Denhardt's solution/0.2 mg/ml salmon sperm DNA/0.2 mg/ml yeast tRNA/20% formamide/labeled probe) is prepared, quenched after boiling and then placed on the tissue slice.

Probe concentration differs according to the tissue, probe, and target gene but is typically used in a range of between 0.5 to 2 ng/µl.

In the case of a dsDNA probe, hybridization solution/probe is boiled. This is to eliminate the secondary structure of the probe. In the case of an oligonucleotide probe, hybridization solution/probe is preferably boiled. Specifically, the lid of a 1.5 ml Eppendorf tube containing the hybridization solution is closed, the tube placed in a stainless steel boiling vessel, the lid closed, and boiling performed for 5 to 7 minutes. Thereafter, the Eppendorf tube is placed directly into a vessel containing ice and water to quench. Then, the Eppendorf tube is placed on ice.

The slide glasses soaked in pre-hybridization fluid is taken out and excess solution around the tissue is wiped off. At this time, care is taken that the tissue does not dry out. Tissue drying is a cause of non-specific signals. Approx. 30 to 70 µl of hybridization solution is then placed on each slide glass and stirred well.

Thereafter, slide glasses on which the hybridization solution was placed are placed in a humid box. A cover is placed thereon to avoid drying, and sealed with vinyl tape, and then it is allowed to stand over night at 37° C.

7. Post-hybridization washing

From the sealed humid box, slides are removed one by one, and placed in a staining vat which contains wash solution. The slides are washed with the following wash solution for 30 minutes each 2 times on a shaker.

Wash solution
2×SSC+0.075% Briji35 (23 Lauryl ether, Sigma)
0.5×SSC+0.075% Briji35

(1-4) Visualization of hybridized probe

In the case of a radioactive label, autoradiography is performed. In the case of a non-radioactive label, an enzyme-antibody method (using an anti-digoxigenin antibody or anti-biotin antibody) probes which hybridize with a target gene (mRNA, DNA) are allowed to develop. Here, detection of a signal according to enzyme antibody methods will be explained.

In the case of labeling with digoxigenin, an anti-digoxigenin antibody is used, but in this case, there are the following three methods: (a) a method using a peroxidase labeled anti-digoxigenin antibody, (b) a method using an alkali phosphatase labeled anti-digoxigenin antibody, and (c) a method using a mouse anti-digoxigenin antibody. Methods (a) and (b) are direct methods, and method (c) is an indirect method further combining a peroxidase- or alkali phosphatase-labeled antibody. Among these, the method with the highest sensitivity is method (b), and the method with the lowest sensitivity is method (a). Even with method (c) it is possible to obtain good sensitivity.

Steps hereafter are the same as normal immunochemical staining and RNase is of no particular concern.

First, pre-hybridization is performed in order to prevent non-specific binding to tissues of the anti-digoxigenin antibody. The pre incubation solution used at this time includes bovine serum albumin, an equivalent scrum in which a primary antibody is prepared, or IgG (if a rabbit antibody, then normal rabbit serum and IgG). Development is usually performed with diaminobenzedine (DAB) and hydrogen peroxide, however, there exist various methods for increasing sensitivity even at this stage. For example, it is possible to increase sensitivity by adding $CoCl_2$ and $NiSO_4(NH_4)_2SO_4$. Further, recently, a kit called Catalyzed Signal Amplification (CSA system, DAKO) has become commercial available, and the sensitivity thereof is extremely good. After developing, nucleus staining is performed. Nucleus staining can be abbreviated where image analysis is performed however it is preferable for clarifying signal negative cells. Where DAB is used as a development pigment, since development with DAB is usually brown, it is preferable to use methyl green staining for nucleus staining since it will be easily visualized.

Table 3 shows the operating steps where a peroxidase labeled anti-digoxigenin antibody is used.

TABLE 3

Post-Hybridization Development: Case where a Peroxidase-labeled Anti-digoxigenin Antibody is used.

1. On the day following hybridization, a methanol block for blocking wash solution, peroxidase within tissue. Immerse in methonal + 0.3% hydrogen peroxide for 20 min at room temperature. Shut out light with aluminum foil. Wash with PBS.
2. Pre-incubation (normal sheep IgG/BSA/PBS) in a humid box, room temperature for over 30 min.
3. Dilute peroxidase labeled sheep anti-digoxigenin antibody with pre-incubation solution 50 to 200 times, and drip onto tissue slices. React for over 1 hour, to overnight, at room temperature in a humid box.
4. Wash with 0.075% Brij 35/PBS. 5 min. 4 times.

TABLE 3-continued

Post-Hybridization Development: Case where a Peroxidase-labeled Anti-digoxigenin Antibody is used.

5. React with DAB, hydrogen peroxide, stain nucleus, dehydrate and encapsulate

When an alkali phosphatase-labeled anti-digoxigenin antibody is used, there are fewer steps and good sensitivity can be obtained. Table 4 shows the operating steps where an alkali phosphatase labeled anti-digoxigenin antibody is used.

TABLE 4

Post-hybridization Development: Where an Alkali Phosphatase-labeled Anti-digoxigenin Antibody is used.

1. After hybridization, wash and then place in buffer solution 1[*1]. 5 min.
2. Pre-incubation: 1 to 1.5% blocking solution/buffer solution 1, 1 hour.
3. Place alkali phosphatase labeled anti-digoxigenin antibody diluted with buffer solution 1, by a factor of 500 to 2,000 on tissue, and react. 30 min to 1 hr.
4. Wash: 15 to 30 min with buffer solution 1, twice, on the shaker.
5. Buffer Solution 2[*2] for 3 min.
6. React with developing solution (NBT 6 μl/ml + BCIP 3.5 μl/ml + levamisole[*3]/buffer solution 21 ml). Watch level of development, and stop reaction[*4].
7. Wash with water, dehydrate, and encapsulate. Where this kit is used, there is little loss of color even after washing, dehydrating and encapsulating. Where another method of developing alkali phosphatase is used, color will easily be lost by washing and dehydrating, so after washing gently, and sponging off water on the tissue, allow to dry, and encapsulate with a water-soluble encapsulating agent.

[*1]100 mM Tris HCl pH 7.5, 150 mM NaCl
[*2]100 mM Tris HCl pH 9.5, 100 mM NaCl, 50 mM $MgCl_2$
[*3]Used to stop non-specific alkali phosphatase development on the tissue. Pre-dissolved solutions such as the one produced by DAKO are available.
[*4]Actual reaction time varies from 5 minutes to around 12 hours.

Here, development with nitro blue tetrazolium (NBT) and 5-bromo-4-chloro-3-indolyl phosphate (BCIP) is indicated. The DIG Nucleic Acid Detection Kit manufactured by Boehringer is convenient.

For reference, the above operations are described in "In situ hybridization techniques", Takehiko Shoji (ed.), Gakusai Kikaku.

In situ hybridization may be performed using Ventana HX system (manufactured by Ventana, Inc.) which realizes full automation. By using this device, it is possible to a large quantity of results with good reproducibility in a short period.

By the above operations, it is possible to examine the state of localization of mRNA expression at the tissue level or at the cell level.

Gene expression localization information obtained as above can be used in searching for a gene related to a condition, in searching for gene or EST which has been cloned but the functions of which is unknown, in genome drug development, etc.

BRIEF DESCRIPTION OF DRAWINGS

FIG. 8 shows the results of analysis by in situ hybridization of distribution of HSP70 expression in brain tissue of a control rat and brain tissue after 2 hours had passed from recovery of blood flow in a brain ischemia model rat.

FIG. 9 shows the results of analysis by in situ hybridization of c-jun expression in brain tissue of a control rat and brain tissue after 2 hours had passed from recovery of blood flow in a brain ischemia model rat.

FIG. 10 shows the results of analysis by in situ hybridization of distribution of EST1 expression in brain tissue of a control rat and brain tissue after 2 hours had passed from recovery of blood flow in a brain ischemia model rat.

FIG. 11 shows magnified views (x250, x500) of FIG. 10.

FIG. 12 shows the results of analysis by in situ hybridization of distribution of EST2 expression in brain tissue of a control rat and brain tissue after 2 hours had passed from recovery of blood flow in a brain ischemia model rat.

BEST MODE FOR CARRYING OUT THE INVENTION

Below, the present invention is explained in detail by use of examples. These Examples are provided to explain the present invention, but not to limit the scope of the present invention

EXAMPLE 1

Figure 1:
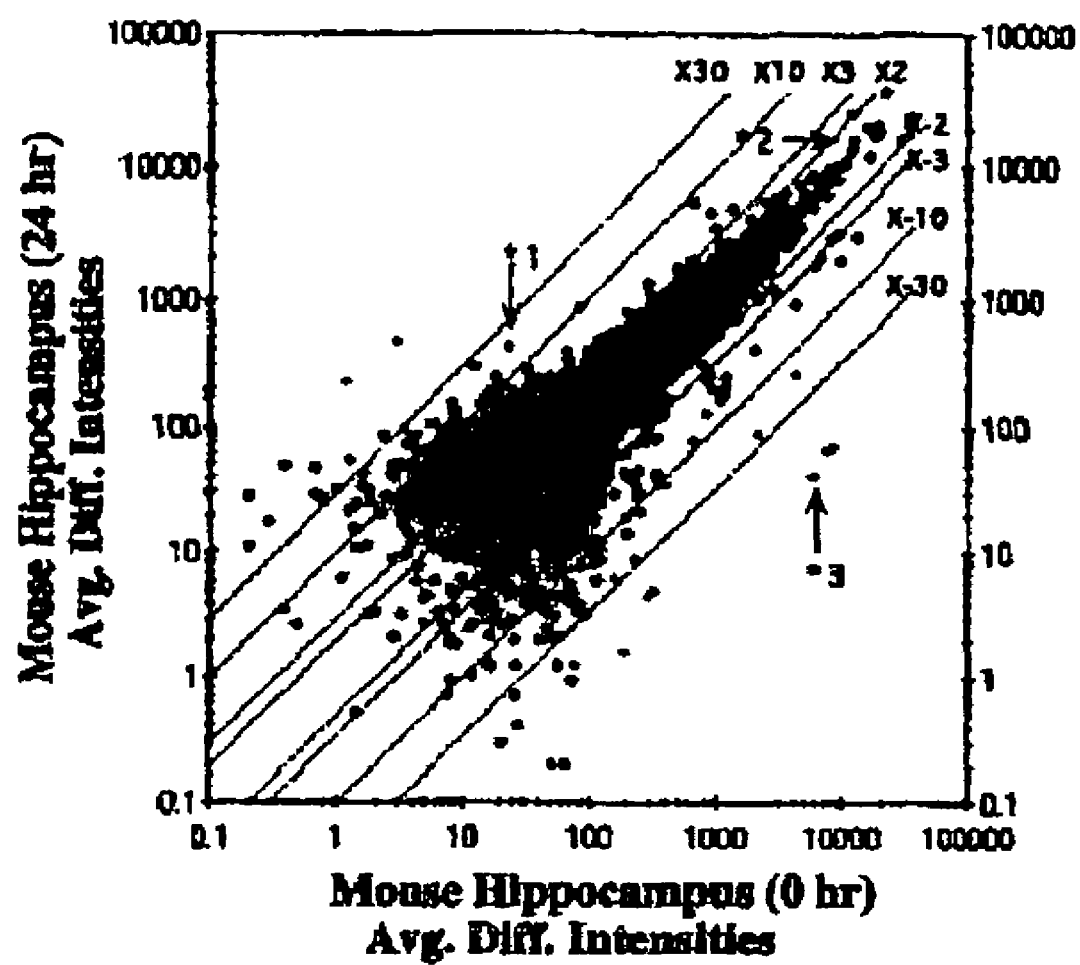
FIG. 1 shows change in expression level in hippocampus of various genes and expression sequence tags after 24 hours had passed since recovery of blood flow in a brain ischemia model rat.

An adult mouse (male, Bcl black, purchased from Sankyo Lab Services) whose common carotid arteries were bilater ally ligated for 20 minutes to interrupt blood flow was adopted as a brain ischemia model. Thereafter, mice were euthanized after passage of time from recovery of blood flow (0 to 24 hours), the hippocampus removed, and a sample prepared according to the protocol. Gene expression analysis was performed using a Mu6,500 Oligonucleotide DNA Probe array with the high-density oligonucleotide array GENECHIP™ system of Affymetrics, Inc. (U.S.). With Mu6,500 Oligonucleotide DNA Probe array, 6500 types of genome could be analyzed simultaneously. Table 1 shows results of analysis using bioinformatics (specifically, a scatter plot by LIMS-EDMT was used) on the basis of this data. The horizontal axis of FIG. 1 shows the genome expression level of a rat (control) in which ischemia processing was not conducted. The vertical axis indicates the genome expression level 24 hours after ischemia/reperfusion. The individual points in FIG. 1 correspond to respective specified genomes. It was possible to differentiate between those where expression level had increased (e.g., in *1, there was an increase in expression of approx. 20 times from 30 to 600 as between before and after ischemia), those for which there was no change (for example, *2), and those which were reduced (for example, in *3, there was a decrease in expression of a factor of approx. {fraction (1/100)} from 7,000 to 70 as between before and after ischemia, and thus we were able to know in general terms about the expression level in the tissue of specific genes. This result confirmed changes in expression level of approximately 1,000 types of genes. If this is connected with publicly available gene information databases, individual genome information can be instantaneously obtained.

EXAMPLE 2

Figure 2:
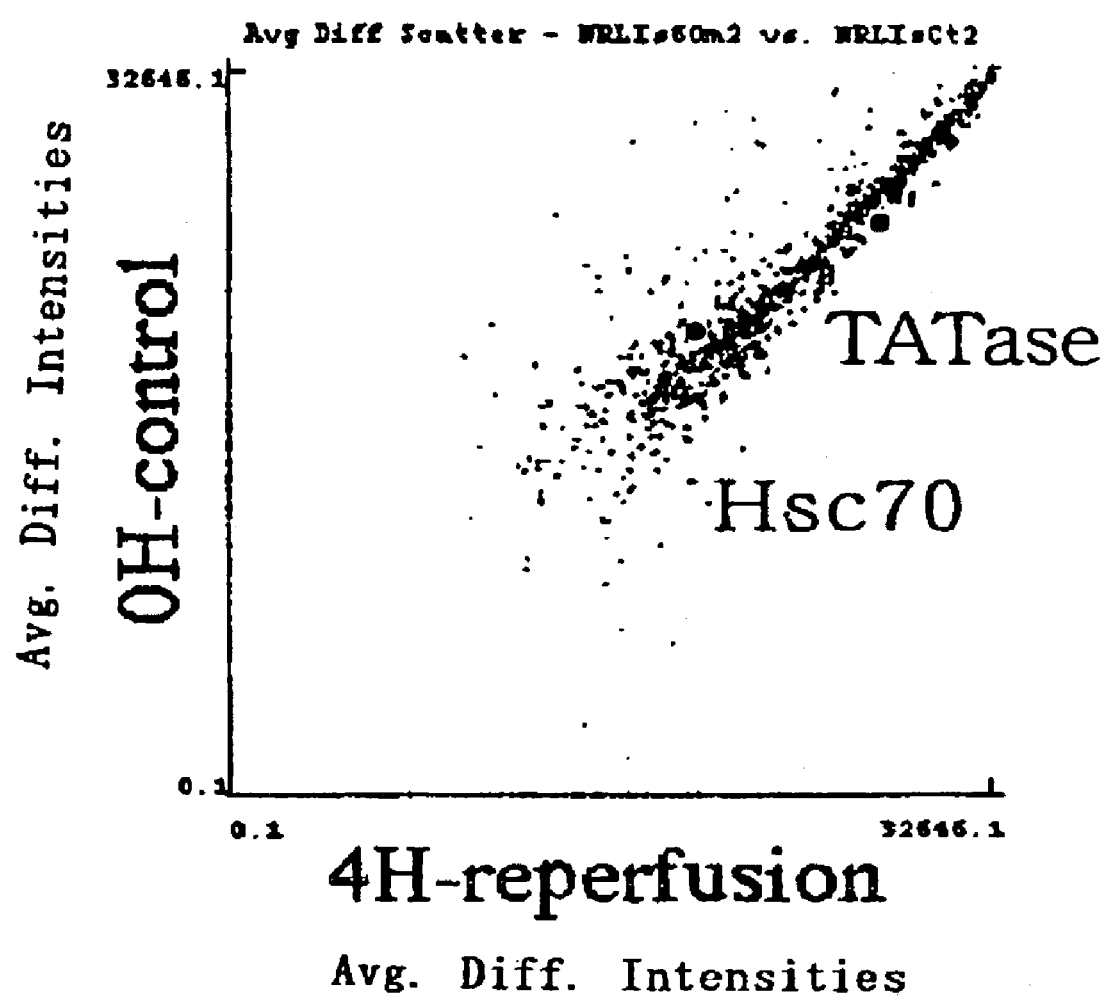
FIG. 2 shows change in expression level in liver of various genes and expression sequence tags after 4 hours had passed since recovery of blood flow in a hepatic ischemia model rat.

An adult rat (male 12-weeks old, Wister-type male rat purchased from Sankyo Lab Services) in which the hepatoportal portion was ligated for 15 minutes to interrupt blood flow, was adopted as a hepatic ischemia model. Thereafter, rats were euthanized after passage of time (0 to 4 hours) after recovery of blood flow, the liver removed and samples prepared according to the protocol. Gene expression analysis was performed using a Rat Toxicology U34 array with the hi-density oligonucleotide array GENECHIP™ system of Affymetrics, Inc. (U.S.). With the Rat Toxicology U34 array, approximately 850 types of rat gene and EST could be analyzed simultaneously. FIG. 2 shows results of analysis using bioinformatics (specifically, a scatter plot by LIMS-EDMT was used) on the basis of this data. The vertical axis of FIG. 2 shows the genome expression level of a rat (control) in which ischemia processing was not conducted. The horizontal axis indicates the genome expression level 4 hours after ischemia/reperfusion. The individual points in FIG. 2 correspond to respective specified genomes. Examples of these include Hsc70 and TATase (Tyrosine aminotransferase). As a result, comparing between 0 hours and 4 hours, there were approximately 100 types where gene expression had increase 2 times or more and approximately 40 types where gene expression had fallen to ½ or less. In respect of Hsc70 and TATase, there was no dominant change in expression level according to GENECHIP™ was exhibited in respect of both genes as between the control group and the ischemia treated.

EXAMPLE 3

Livers were removed respectively from a control rat and the hepatic ischemia model rat (after 4 hours had passed since recovery of blood flow) of Example 2 and fresh frozen slices were prepared. Using Digoxigenin-labeled position 229–629 (400 bp) of HSC70 (Neat shock protein 70-like protein, NCBI GenBank Accession No. M11942) as an RNA probe, in situ hybridization of the fresh frozen slices was performed with Ventana HX system. Primer sequences used in preparation of RNA probes are shown in Table 5 and in situ hybridization conditions are shown in Table 6.

TABLE 5

| No. | Upper Primer | Position | Lower Primer | Position | Length |
|---|---|---|---|---|---|
| HSC70 (heat shock protein 70 like protein) | | | | | |
| M11942 | CAATGAACCCCACCAACACAG (SEQ ID NO:1) | 229 | CTTTCAGCCCCGACTTCTTA (SEQ ID NO:2) | 629 | 400 bp |
| HSP70 | | | | | |
| L16764 | GCTGGTGGGCGGCTCGAC (SEQ ID NO:3) | 1182 | GCTCTTGTCCGTGGCCGTGAC (SEQ ID NO:4) | 1659 | 478 bp |
| TATase | | | | | |
| X02741 | GAAGAAAGAAAGGCAGGAAGG (SEQ ID NO:5) | 192 | CTTGGAATGAGGATGTTTTGT (SEQ ID NO:6) | 594 | 403 bp |
| c-jun | | | | | |
| X17163 | TGAAGCAGAGCATGACCTTG (SEQ ID NO:7) | 453 | AGTTGCTGAGGTTGGCGTAG (SEQ ID NO:8) | 878 | 426 bp |
| EST 1 | | | | | |
| AA818604 | GCGATCTCCTTCATCTTGGT (SEQ ID NO:9) | 147 | GACTTGGGCACCACCTACTC (SEQ ID NO:10) | 511 | 365 bp |

TABLE 5-continued

| No. | Upper Primer | Position | Lower Primer | Position | Length |
|---|---|---|---|---|---|
| | | EST 2 | | | |
| A1103915 | TGGGCTCAAAGCCATATTTC (SEQ ID NO:11) | 183 | CCGAACTCTAGAGCCACCAG (SEQ ID NO:12) | 585 | 403 bp |

TABLE 6

| Step | Reagent | Temp. | Time |
|---|---|---|---|
| Off line | | | |
| Fixation | 4% PFA/PBS | R.T. | 30 min |
| Wash | PBS | R.T. | 5 min × 2 times |
| DEPC treatment | 0.1% DEPC/PBS | R.T. | 15 min × 2 times |
| Wash | PBS | R.T. | 1 min |
| | $H_2O$ | R.T. | 1 min |
| Acid treatment | 0.2M HCl | R.T. | 20 min |
| Wash | $H_2O$ | R.T. | 1 min |
| | PBS | R.T. | 3 min × 3 times |
| | $5_x$ SSC | R.T. | 30 min |
| Probe | App. 200 µL 50% FA, $5_x$ SSC, $5_x$ Denhardt's, 500 ug/ml ssDNA, 250 ug/ml t-RNA, 1 mM DTT | | |
| Denaturation | | 65° C. | 15 min |
| Hybridization | | 57° C. | 14 hrs |
| Stringency Wash | | | |
| $1^{st}$–$2^{nd}$ | 2 × SCC | 55° C. | 6 min × 2 times |
| $3^{rd}$–$4^{th}$ | 0.1 × SSC | 55° C. | 16 min × 2 times |
| Antibody Blocking | Protein Brock | 37° C. | 20 min |
| Antibody | Serum-Free × 2000 anti DIG-AP | 37° C. | 46 min |
| Wash | TBS | R.T | 10 min × 3 times |
| | APB | R.T | 5 min |
| Detection | BM-Purple | R.T | 6 hrs~ |

Figure 3:
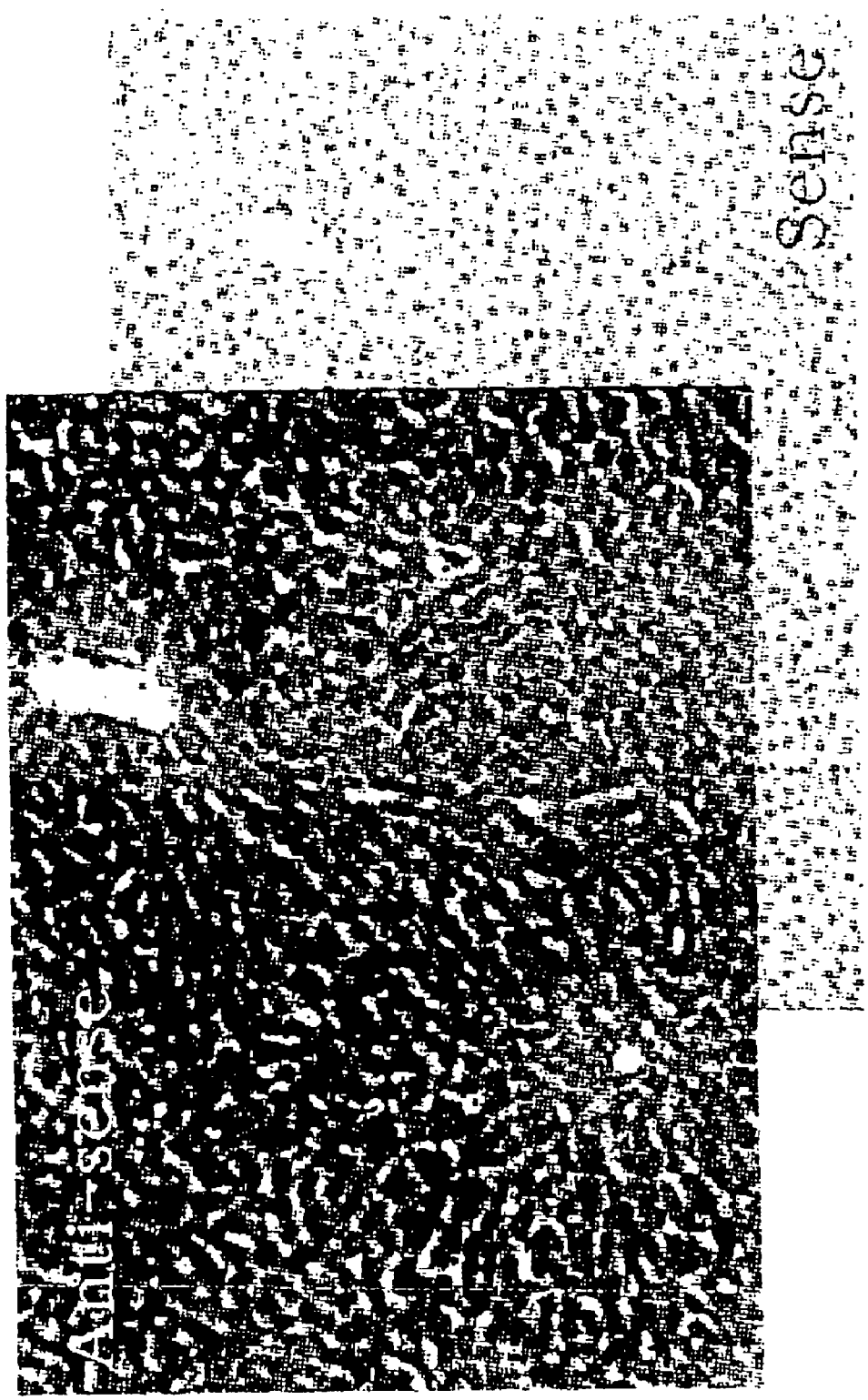
FIG. 3 shows results of analysis by in situ hybridization of distribution of Hsc70 expression in liver tissue of a control rat.
Figure 4:
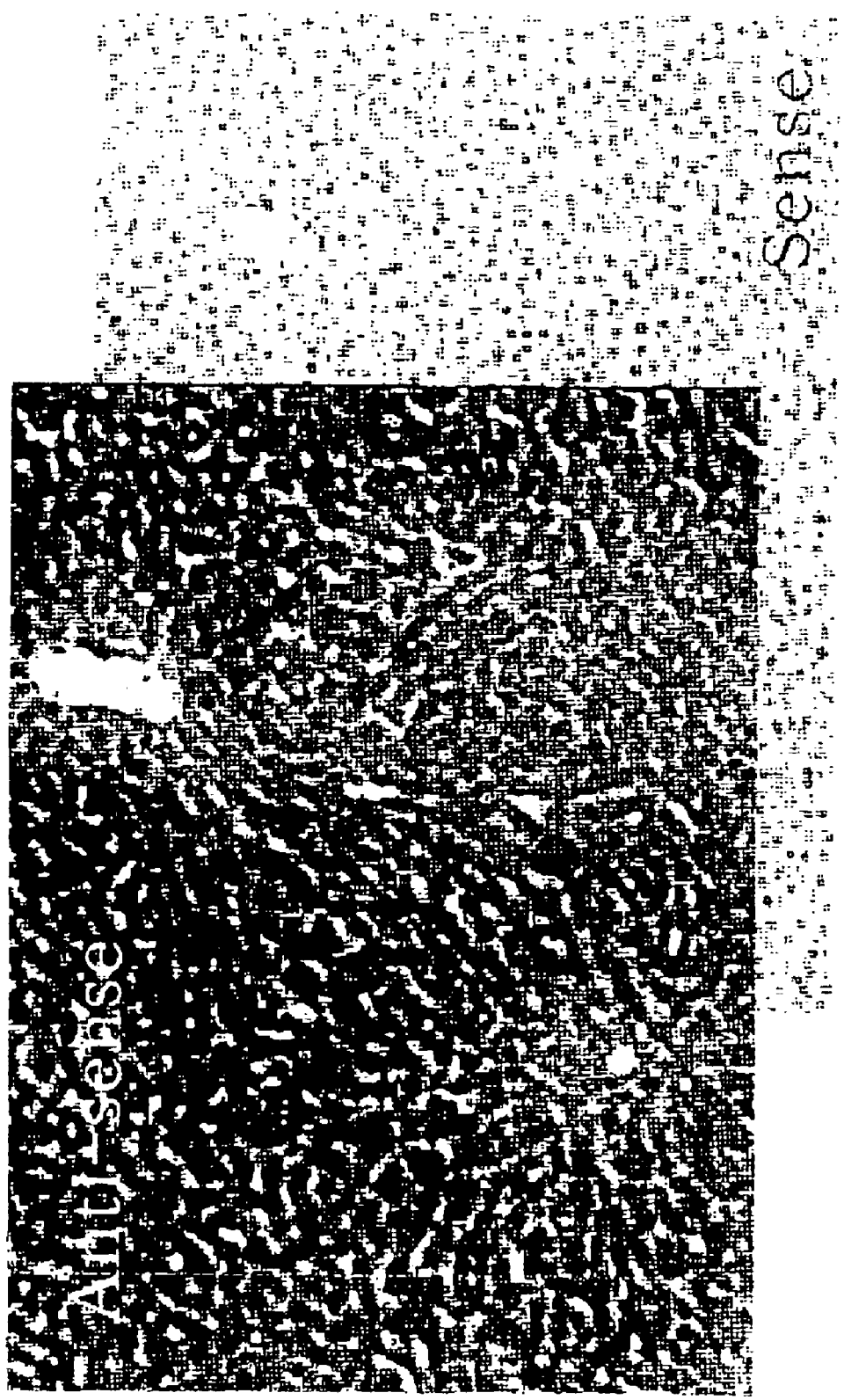
FIG. 4 shows results of analysis by in situ hybridization of distribution of Hsc70 expression in liver tissue after 4 hours had passed since recovery of blood flow in a hepatic ischemia model rat.

Results for the control rat are shown in FIG. 3, and results for the hepatic ischemia model rat are shown in FIG. 4. Within the figures, Anti-sense shows the results of staining with antisense probe, and Sense indicates results of staining with sense probe. Comparing FIGS. 3 and 4, it was clear that in the liver tissue of the hepatic ischemia model rat, there was good staining around the central veins (the hole portion of FIG. 4) (expression of HSC70 was high), and staining became fainter with distance (expression of HSC70 was falling). From this, it can be said that in respect of HSC70, ischemia exhibited an effect around the central nerves.

EXAMPLE 4

Using a TATase probe instead of a HSC70 probe, in situ hybridization was performed according to similar steps to those of Example 3. As a TATase probe, position 192–594 (403 bp) of TATase (NCBI GenBank Accession No. X02741) labeled with digoxigenin was used. Primer sequences used in preparation of RNA probes are shown in Table 5 and in situ hybridization conditions are as shown in Table 6.

Figure 5:
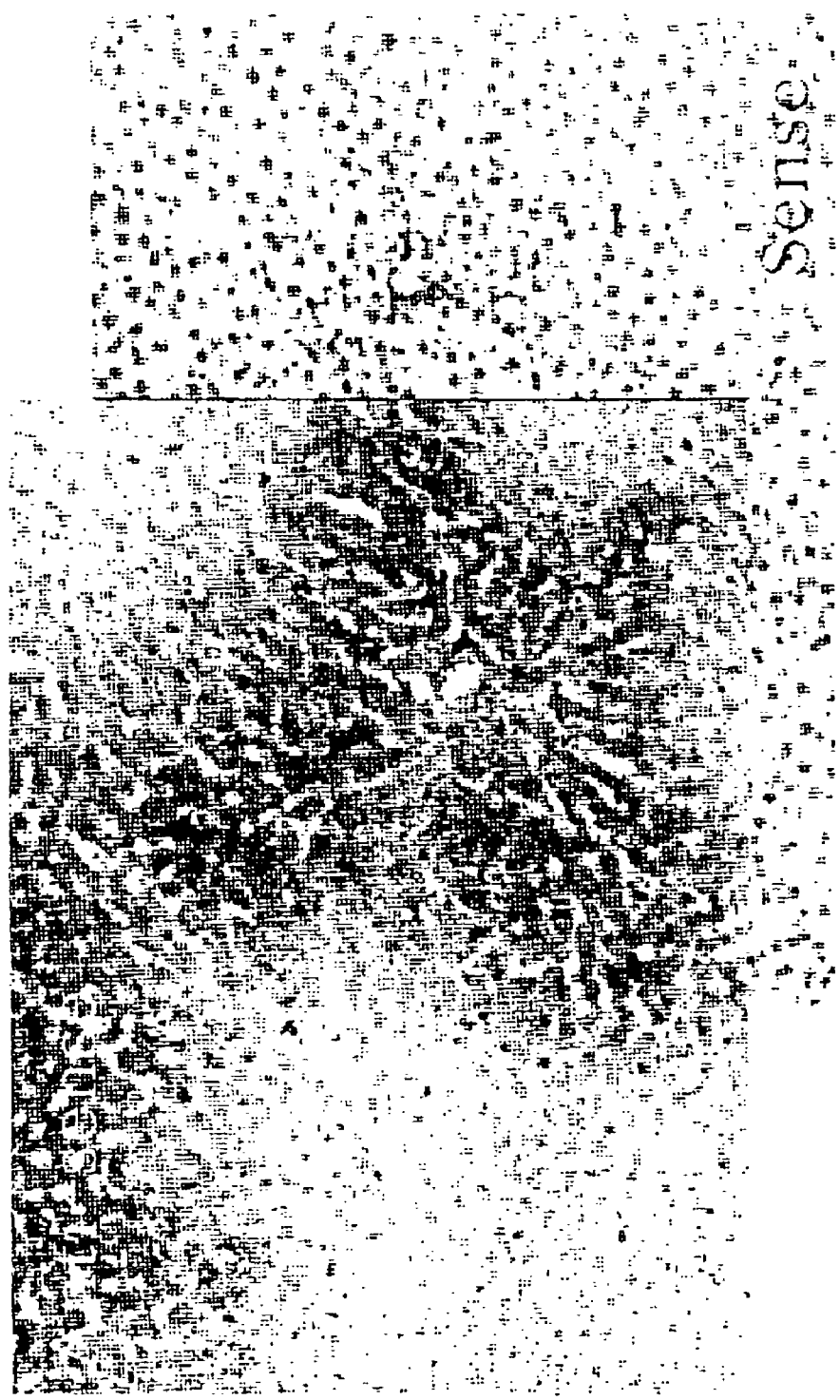
FIG. 5 shows results of analysis by in situ hybridization of distribution of TATase expression in liver tissue of a control rat.
Figure 6:
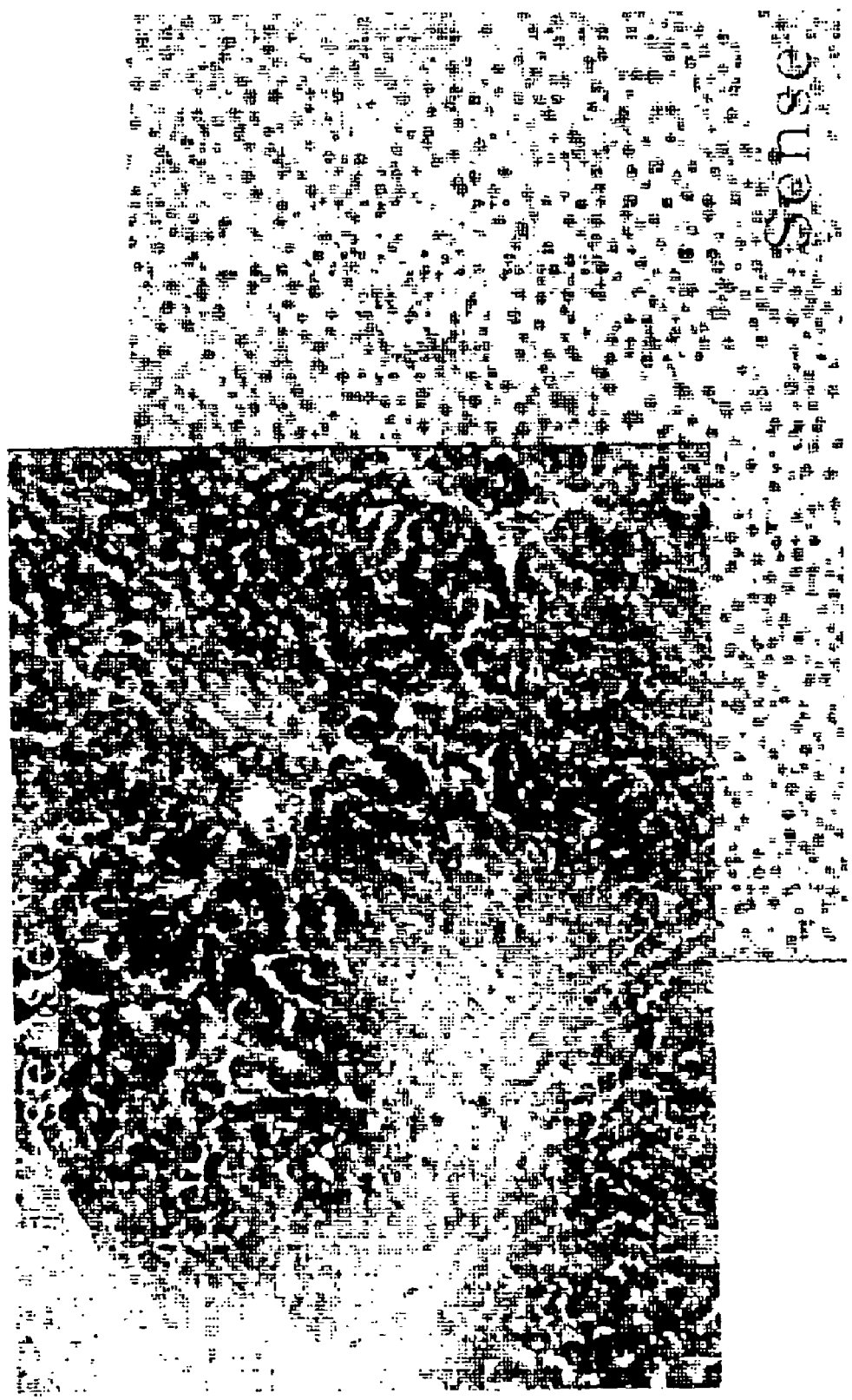
FIG. 6 shows results of analysis by in situ hybridization of distribution of TATase expression in liver tissue after 4 hours had passed since recovery of blood flow in a hepatic ischemia model rat.

Results for the control rat are shown in FIG. 5, and results for the hepatic ischemis model rat are shown in FIG. 6. Within the figures, Anti-sense shows the results of staining with antisense probe, and Sense indicates results of staining with sense prove. Comparing 5 and 6, it was clear that in the liver tissue of the hepatic ischemia model rat, there was good staining around the central veins (the hole portion of FIG. 6) (expression of TATase was high), and staining became fainter with distance (expression of TATase was falling). From this, it can be said that in respect of TATase, ischemia exhibited an effect around the central nerves.

Regarding Hsc70 and TATase, the expression level according to GENECHIP™ of both genes in both the control group, ischemia processed group exhibit no particular dominance. However, with in situ hybridization, it is clear that expression around the central vein increased as between before and after ischemia. Further, it was clear that this change was markedly appearing due: to TATase. Thus, by combining GENECHIP™ and in situ hybridization, information regarding a greater number of genes can be obtained.

EXAMPLE 5

Figure 7:
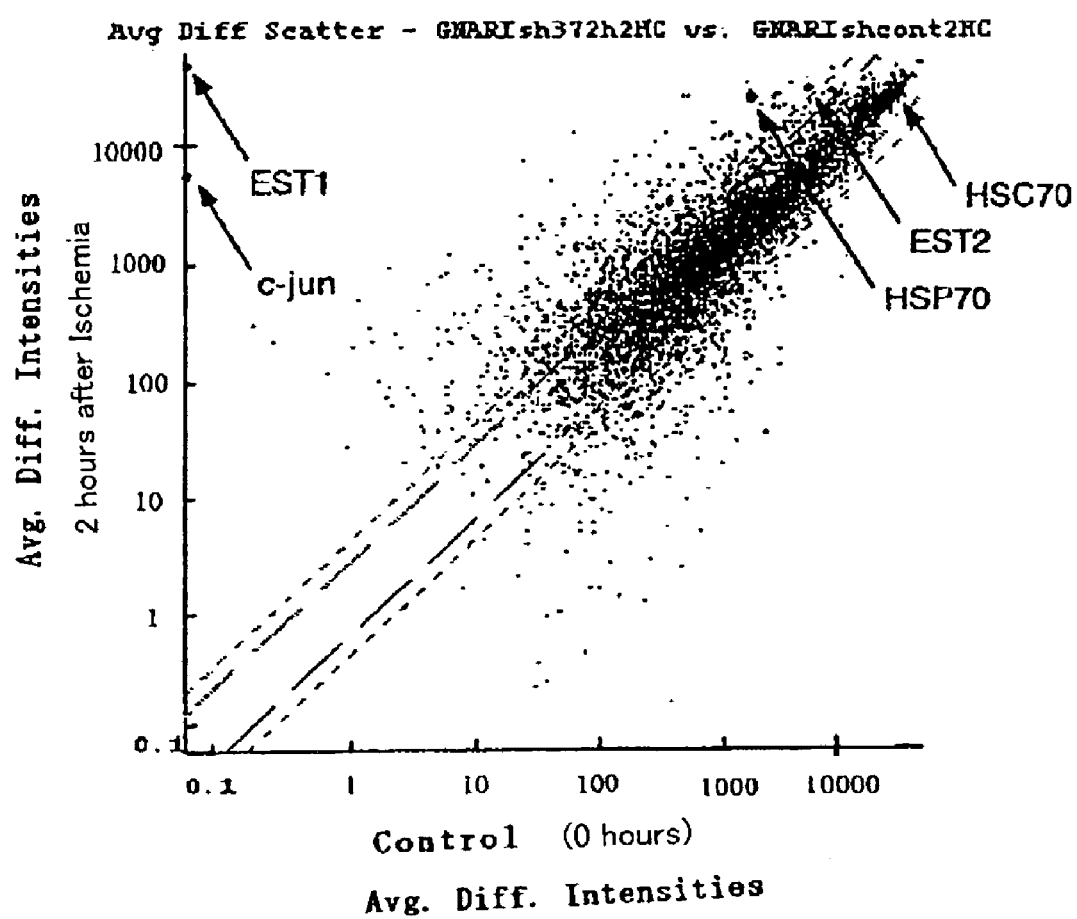
FIG. 7 shows change in expression levels of various genes and expression sequence tags in the brain of a brain ischemia model rat after 2 hours had passed since recovery of blood flow. Expression levels of HSC70, HSP70, c-jun, EST1 and EST2 are clearly shown.

An adult rat (male, Wister-Kyoto, 12-weeks old, purchased from Sankyo Lab Service) whose bilateral body temperature and brain temperature was maintained at 37 degree. C., whose common carotid arteries were bilaterally ligated for 10 minutes to interrupt blood flow, and further whose blood pressure was reduced to 30 to 40 mmHg, was adopted as a brain ischemia model (generally known as, Smith's brain ischemia model). After 10 minutes, reperfusion was allowed, and brain temperature and body temperature were maintained at 37° C. After 2 hours, the rat was euthanized, the hippocampus removed and a sample prepared following the protocol. Using rat U34 array, gene expression analysis was perform with GENECHIP™ system of Affymetrics, Inc. (United States). With a rat U34 array, it was possible to analyze 34,000 types of genome simultaneously. FIG. 7 shows results of analysis using bioinformatics (specifically, a scatter plot by LIMS-EDMT was used) on the basis of this data. FIG. 7, is a figure showing a scatter plot in respect of change in 34000 genes in a control group and 2 hours after ischemia. The horizontal axis of FIG. 7 shows the genome expression level of a rat (control) in which ischemia processing was not conducted. The vertical axis indicates the genome expression level 2 hours after ischemia/reperfusion. The individual points in Figure correspond to respective specified genomes. Examples of these include HSC70, HSP70, c-jun EST1 and EST2. Points lying on the X-Y line indicate that there was no change in the corresponding genes between before and after processing. As a result, comparing between 0 hours and 2 hours, there were approximately 475 types where gene expression had increase 2 times or more, and approximately 486 types where gene expression had fallen to ½ or less. In respect of HSC70, there was no change between before and after ischemia. (Intensity change Control*OH: approximately 30,000 ischemia*2H: approximately 30,000). HSP70 exhibited an increase in expression of as much as 20 times as between before and after ischemia (Intensity change Control*OH: approx. 1,000*ischemia*2H: approx. 20,000). c-jun was hardly expressed at all prior to ischemia but after ischemia there was a dramatic increase in the expression thereof (Intensity change Control*OH: approx. 0.1→ischemia*2H: approx. 20,000). EST 1 was hardly expressed at all prior to ischemia but after ischemia there was a dramatic increase in the expression thereof (Intensity change Control*OH: approx. 3,000→ischemia*2H: approx. 15,000). EST2 exhibited an increase in expression of as much as 5 times as between before and after ischemia (Change in intensity Control *OH: approx. 3,000→ischemia*2H: approx. 15,000).

EXAMPLE 6

Brains were removed respectively from a control rat and the brain ischemia model rat of Example 5 (after 2 hours had passed since recovery of blood flow), and fresh frozen slices were prepared. Digoxigenin-labeled position 1182–1659 (478 bp) of HSP70 (Heat shock protein 70 like protein, NCBI GenBank Accession No. L16764) was used as an RNA probe and in situ hybridization of brain fresh frozen slices was performed. Primer sequences used in preparation of RNA probes are shown in Table 5 and in situ hybridization conditions are as shown in Table 6.

Results for the control rat and brain ischemia model rat are shown in FIG. 8. Within the figures, anti-sense shows the results of staining with antisense probe, and sense indicates results of staining with sense probe. Diffuse expression of HSP70 in the whole brain had increased. In particular, expression thereof increased markedly in the hippocampus. This matched with GENECHIP™ data and therefore provides support for the data obtained with GENECHIP™.

EXAMPLE 7

Using c-jun probe instead of HSP70 probe, in situ hybridization was performed according to steps similar to those of Example 6. As a c-jun probe, digoxigenin-labeled position 453–878 of c-jun (426 bp) (NCBI GenBank Accession No.X17163) was used. Primer sequences used in preparation of RNA probes are shown in Table 5 and in situ hybridization conditions are as shown in Table 6.

Results for the control rat and the brain ischemia model rat are shown in FIG. 9. Within the figures, anti-sense shows the results of staining with antisense probe, and sense indicates results of staining with sense probe. Diffuse expression of c -jun in the whole brain was increasing. This, in respect of the point that there had been no expression, but as a result of ischemia, there was a dramatic increase, matched with GENECHIP™ data and therefore provides support for the data obtained with GENECHIP™.

EXAMPLE 8

Using an EST1 probe instead of an HSP70 probe, in situ hybridization was performed according to steps similar to those of Example 6. As an EST1 probe, digoxigenin-labeled position 147–511 (365 bp) of EST1 (NCBI GenBank Accession No.AA818604) was used. Printer sequences used in preparation of RNA probes arc shown in Table 5 and in situ hybridization conditions are as shown in Table 6.

Results for the control rat and the brain ischemia model rat are shown in FIG. 10. Within the figures, anti-sense shows the results of staining with antisense probe, and sense indicates results of staining with sense probe.

Further magnified views of the results for the control rat and the brain ischemia model rat are shown in FIG. 11.

For EST1, deep staining was recognized in the hippocampus of the brain at low magnification in the dentate gyros and choroids layer of the brain ventricle. Viewing with a microscopic magnification of 250x, 500x, it was clear that there was no expression prior to ischemia but after ischemia, cells of the internal skin of blood vessels were markedly stained. In this way, it is possible not only to specify differences in brain distribution, but also differences in cell type within a tissue.

EXAMPLE 9

Using an EST2 probe instead of an HSP70 probe, in situ hybridization was performed according to steps similar to those of Example 6. As a EST2 probe, digoxigenin-labeled position 183–585 (403 bp) of EST2 (NCBI GenBank Accession No. AI103915) was used. Primer sequences used in preparation of RNA probes are shown in Table 5 and in situ hybridization conditions are as shown in Table 6.

Results for the control rat and the brain ischemia model rat are shown in FIG. 12. Within the figure, anti-sense shows the results of staining with antisense probe, and sense indicates results of staining with sense probe. For EST2, deep staining of hippocampus cone cells, before and after ischemia in the brain, suggesting an increase in expression.

EFFECT OF THE INVENTION

The method of screening genes according to the method present invention involves the innovative approach of selecting a gene from the novel point of view of localization of a gene and/or expression sequence tag in the tissue or cells of an organists, and is useful in narrowing down on a target gene.

SEQUENCE LISTING FREE TEXT

SEQ ID NO: 1: Nucleotide sequence of an upstream primer targeting the sequence from position 229 to 629 of HSC70.

SEQ ID NO: 2: Nucleotide sequence of a downstream primer targeting the sequence from position 229 to 629 of HSC70.

SEQ ID NO: 3: Nucleotide sequence of an upstream primer targeting the sequence from position 1182. to 1659 of HSP70.

SEQ ID NO: 4: Nucleotide sequence of a downstream primer targeting the sequence from position 1182 to 1659 of HSC70.

SEQ ID NO: 5: Nucleotide sequence of an upstream primer targeting the sequence from position 192 to 594 of TATase.

SEQ ID NO: 6: Nucleotide sequence of a downstream primer targeting the sequence from position 192 to 594 of TATase.

SEQ ID NO: 7: Nucleotide sequence of an upstream primer targeting the sequence from position 453 to 878 of c-jun.

SEQ ID NO: 8: Nucleotide sequence of a downstream primer targeting the sequence from position 453 to 878 of c-jun.

SEQ ID NO: 9: Nucleotide sequence of an upstream primer targeting the sequence from position 147 to 511 of EST1.

SEQ ID NO: 10: Nucleotide sequence of a downstream primer targeting the sequence from position 147 to 511 of EST1.

SEQ ID NO: 11: Nucleotide sequence of an upstream primer targeting the sequence from position 183 to 585 of EST2.

SEQ ID NO: 12: Nucleotide sequence of a downstream primer targeting the sequence from position 183 to 585 of EST2.

---

What is claimed is:

1. A method of screening to identify a gene whose function is unknown previously, as a target for drug development, which comprises:
   (a) examining the expression of mRNAs and/or expression sequence tags being, products of gene expression before and after an event by using a high-density oligonucleotide array, and making a scatter diagram showing changes in expression levels of the mRNAs and/or expression sequence tags between before and after the event,
   (b) determining one or more specific mRNAs and/or expression sequence tags whose expression has changed in response to the event, from the results in the scatter diagram and from databases searches,
   (c) for each of said one or more mRNAs and/or expression sequence tags whose expression has changed in response to the event, designing a probe that will specifically hybridize with the mRNA and/or expression sequence tag
   (d) performing in situ hybridization of at least two types of tissues or cells of an organism before and after the event by using the one or more probes designed in step (c),
   (e) examining the localization of the one or more mRNAs and/or expression sequence tags in the tissues or cells before and after the event,
   (f) determining whether the localization of those mRNAs and/or expression sequence tags has changed in response to the event, and
   (g) identifying those mRNAs and/or expression sequence tags whose expression and localization have both changed in response to the event as a target for drug development.

2. The method according to claim 1, wherein the mRNA and/or expression sequence tag is expressed in cultured cells or tissue.

3. The method according to claim 1, wherein the gene encoding the mRNA and/or expression sequence tag has been cloned.

4. The method according to claim 1, wherein the localization of at least two different mRNAs and/or expression sequence tags is determined in a single screening of the tissue or cell.

5. The method according to claim 1, wherein the gene encodes a substance effective as a drug.

6. The method according to claim 1, wherein the gene is related to a disease.

7. The method according to claim 1 comprising, after step (g), the step of determining the function of the gene.

8. The method according to claim 1, wherein the tissue or cell is collected from an organism at two or more different points in time after occurrence of an event.

9. The method according to claim 1 or 8, wherein the event is ischemia or cancer.

* * * * *

SEQUENCE LISTING

```
<160> NUMBER OF SEQ ID NOS: 12

<210> SEQ ID NO 1
<211> LENGTH: 21
<212> TYPE: DNA
<213> ORGANISM: Artificial Sequence
<220> FEATURE:
<223> OTHER INFORMATION: Description of Artificial Sequence:Synthetic
      DNA

<400> SEQUENCE: 1
caatgaaccc caccaacaca g                                              21

<210> SEQ ID NO 2
<211> LENGTH: 20
<212> TYPE: DNA
<213> ORGANISM: Artificial Sequence
<220> FEATURE:
<223> OTHER INFORMATION: Description of Artificial Sequence:Synthetic
      DNA

<400> SEQUENCE: 2
ctttcagccc cgacttctta                                                20

<210> SEQ ID NO 3
<211> LENGTH: 18
<212> TYPE: DNA
<213> ORGANISM: Artificial Sequence
<220> FEATURE:
<223> OTHER INFORMATION: Description of Artificial Sequence:Synthetic
      DNA

<400> SEQUENCE: 3
gctggtgggc ggctcgac                                                  18

<210> SEQ ID NO 4
<211> LENGTH: 21
<212> TYPE: DNA
<213> ORGANISM: Artificial Sequence
<220> FEATURE:
<223> OTHER INFORMATION: Description of Artificial Sequence:Synthetic
      DNA

<400> SEQUENCE: 4
gctcttgtcc gtggccgtga c                                              21

<210> SEQ ID NO 5
<211> LENGTH: 21
<212> TYPE: DNA
<213> ORGANISM: Artificial Sequence
<220> FEATURE:
```

<223> OTHER INFORMATION: Description of Artificial Sequence:Synthetic
      DNA

<400> SEQUENCE: 5
gaagaaagaa aggcaggaag g                                              21

<210> SEQ ID NO 6
<211> LENGTH: 21
<212> TYPE: DNA
<213> ORGANISM: Artificial Sequence
<220> FEATURE:
<223> OTHER INFORMATION: Description of Artificial Sequence:Synthetic
      DNA

<400> SEQUENCE: 6
cttggaatga ggatgttttg t                                              21

<210> SEQ ID NO 7
<211> LENGTH: 20
<212> TYPE: DNA
<213> ORGANISM: Artificial Sequence
<220> FEATURE:
<223> OTHER INFORMATION: Description of Artificial Sequence:Synthetic
      DNA

<400> SEQUENCE: 7
tgaagcagag catgaccttg                                                20

<210> SEQ ID NO 8
<211> LENGTH: 20
<212> TYPE: DNA
<213> ORGANISM: Artificial Sequence
<220> FEATURE:
<223> OTHER INFORMATION: Description of Artificial Sequence:Synthetic
      DNA

<400> SEQUENCE: 8
agttgctgag gttggcgtag                                                20

<210> SEQ ID NO 9
<211> LENGTH: 20
<212> TYPE: DNA
<213> ORGANISM: Artificial Sequence
<220> FEATURE:
<223> OTHER INFORMATION: Description of Artificial Sequence:Synthetic
      DNA

<400> SEQUENCE: 9
gcgatctcct tcatcttggt                                                20

<210> SEQ ID NO 10
<211> LENGTH: 20
<212> TYPE: DNA
<213> ORGANISM: Artificial Sequence
<220> FEATURE:
<223> OTHER INFORMATION: Description of Artificial Sequence:Synthetic
      DNA

<400> SEQUENCE: 10
gacttgggca ccacctactc                                                20

<210> SEQ ID NO 11
<211> LENGTH: 20
<212> TYPE: DNA
<213> ORGANISM: Artificial Sequence
<220> FEATURE:
<223> OTHER INFORMATION: Description of Artificial Sequence:Synthetic

```
                           DNA

<400> SEQUENCE: 11
tgggctcaaa gccatatttc                                              20

<210> SEQ ID NO 12
<211> LENGTH: 20
<212> TYPE: DNA
<213> ORGANISM: Artificial Sequence
<220> FEATURE:
<223> OTHER INFORMATION: Description of Artificial Sequence:Synthetic
      DNA

<400> SEQUENCE: 12
ccgaactcta gagccaccag                                              20
```